United States Patent [19]

Stoltefuss

[11] Patent Number: 5,270,469

[45] Date of Patent: Dec. 14, 1993

[54] PROCESS OF PREPARING 3-PHENYL-QUINOLINE-5-CARBOXYLIC ACID

[75] Inventor: Jürgen Stoltefuss, Haan, Fed. Rep. of Germany

[73] Assignee: Bayer Aktiengesellschaft, Leverkusen, Fed. Rep. of Germany

[21] Appl. No.: 971,030

[22] Filed: Nov. 3, 1992

Related U.S. Application Data

[62] Division of Ser. No. 757,865, Sep. 11, 1991, Pat. No. 5,210,231.

[30] Foreign Application Priority Data

Sep. 20, 1990 [DE] Fed. Rep. of Germany ....... 4029807

[51] Int. Cl.$^5$ ............................................ C07D 215/14
[52] U.S. Cl. ..................................... 546/170; 549/304
[58] Field of Search .......................... 549/304; 546/170

[56] References Cited

U.S. PATENT DOCUMENTS

| 4,730,056 | 3/1988 | Lowe, III | 548/472 |
| 5,130,434 | 7/1992 | Hagen et al. | 546/170 |

FOREIGN PATENT DOCUMENTS

| 2705414 | 8/1977 | Fed. Rep. of Germany . | |
| 0174769 | 9/1985 | Japan | 546/170 |
| 0831561 | 3/1960 | United Kingdom | 546/170 |

OTHER PUBLICATIONS

Chemical Abstracts, vol. 78, No. 1, Jan. 8, 1973, Columbus, Ohio, USA Watanabe, Tokuhiro et al. "Indoles, III. New synthesis of 4-indolecarboxylic acid." p. 339, col. 1, para. No. 4 058h.

Chemical Abstracts, vol. 80, No. 25, Jun. 1974, Columbus, Ohio, USA Aoki, Katsumichi et al., "Fungicidal compositions containing 4-chlorophthalide derivatives." p. 84, col. 2, para. No. 141791x.

Chemical Abstracts, vol. 90, No. 23, Jun. 4, 1979, Columbus, Ohio, USA Houbion, J. A. et al. "The synthesis of unamiguously substituted 3-hydroxyphthalides." p. 640, col. 2, para. No. 186 703t.

Chemical Abstracts, vol. 104, No. 1, Jan. 6, 1986, Columbus, Ohio, USA Sloan, Kenneth B. et al. "Further reactions of 3-hydroxy-1(3H)-isobenzofuranone with amines." p. 523, col. 1 para. No. 5 724q.

J. Org. Chem. 1988, 53, 223-224.
J. Org. Chem. 1988, 53, 1199-1202.
J. of Med. Chem., 1988, vol. 31, No. 4, 824-830.
T. Watanabe et al., Chem. Pharm. Bull, 20(10), 2123-2127 (1972).

Primary Examiner—C. Warren Ivy
Assistant Examiner—A. Owens
Attorney, Agent, or Firm—Sprung Horn Kramer & Woods

[57] ABSTRACT

A process for preparing 3-phenyl-quinoline-5-carboxylic acid comprising reacting 4-amino-3-hydroxyphthalide with phenylacetaldehyde.

1 Claim, No Drawings

PROCESS OF PREPARING 3-PHENYL-QUINOLINE-5-CARBOXYLIC ACID

This is a division, of application Ser. No. 07/757,865, filed Sep. 11, 1991, now U.S. Pat. No. 5,210,231.

The present invention relates to 4-amino-3-hydroxyphthalide, an important intermediate for the synthesis of 3-substituted-5-quinoline-carboxylic acids and to a process for its preparation.

3-Hydroxyphthalides which are substituted in the phenyl ring, optionally polysubstituted, by chlorine, carboxyl or methoxy, are known from the publications J. Org. Chem. 1988, 53, 223–224; 53, 1199–1202 and J. of Med. Chem., 1988, Vol. 31, No. 4, 824–830.

The present invention relates to the new compound 4-amino-3-hydroxyphthalide of the formula (I).

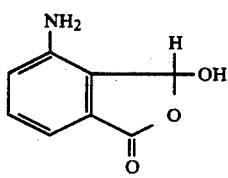

The invention furthermore relates to a process for the preparation of the compound of the formula (I), characterised in that 4-Nitro-3-hydroxyphthalide of the formula (II)

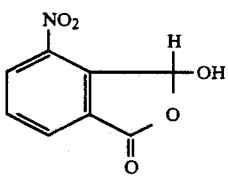

is reduced in inert solvents, preferably by hydrogenation, in the presence of a catalyst.

The process can be illustrated by the following equation:

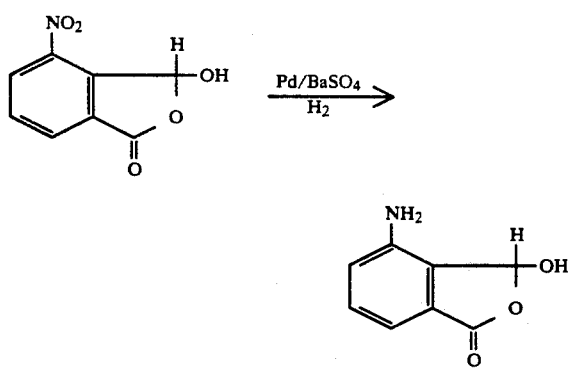

Suitable solvents for the hydrogenation are all organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphorous triamide or dimethylformamide, or acetic acid and methylene chloride, carbon tetrachloride or toluene. It is also possible to use mixtures of the solvents mentioned. Methanol, ethanol, propanol or tetrahydrofuran are preferred.

The hydrogenation can be carried out at normal pressure or at elevated pressure, for example from 0.5 to 5 bar, preferably at atmospheric pressure.

The reduction is in general carried out in a temperature range from 0° C. to 80° C., in the case of hydrogenation preferably at room temperature.

Suitable catalysts are platinum, palladium, palladium/animal charcoal, palladium/barium sulphate or Raney nickel. Palladium/barium sulphate is particularly suitable.

The catalyst is employed in an amount from 0.00001 to 1 mol, preferably from 0.001 to 0.1 mol, relative to 1 mol of the compound of the formula (II).

The compounds of the formula (II) are known [cf. T. Watanabe et al., Chem. Pharm. Bull, 20 (10), 2123–2127 (1972)].

The above preparation process is only given for clarification. The preparation of the compound of the formula (I) according to the invention is not restricted to this process, but any modifications of this process, for example the use of nitro-amino reduction methods known from the literature, are utilisable in the same manner for the preparation of the compound according to the invention.

The compound according to the invention is a useful intermediate for the direct preparation of 3-substituted quinoline-5-carboxylic acids, which are known in some cases or are new, which are used in turn as starting substances for the corresponding 3-substituted quinoline-5-aldehydes and are thus of great importance in 1,4dihydropyridine chemistry.

PREPARATION EXAMPLES

EXAMPLE 1

4-Amino-3-hydroxyphthalide

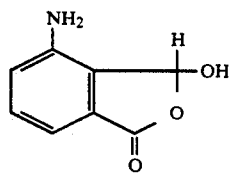

10 g of 3-hydroxy-4-nitro-phthalide are dissolved in 100 ml of tetrahydrofuran and, after addition of 1 g of palladium on barium sulphate (5%), the mixture is hydrogenated at atmospheric pressure and 20°–25° C. The catalyst is filtered off and the filtrate is concentrated. The evaporation residue is stirred with ether and filtered off with suction. 5.8 g (68.5% of theory) of a colourless substance of melting point 280°–285° C. (dec.) are obtained.

EXAMPLE 2

3-Phenyl-Quinoline-5-Carboxylic Acid

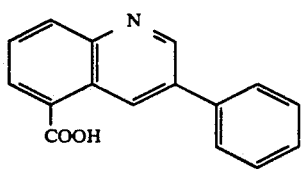

50 g (0.256 mol) of 3-hydroxy-4-nitro-phthalide are hydrogenated at 20° C. and 3 bar in 380 ml of ethanol using 5 g of palladium/barium sulphate (5%). The catalyst is filtered off with suction, and 0.308 mol (38.7 ml) of phenylacetaldehyde is added to the filtrate. The mixture is boiled for 4 hours, the quinolinecarboxylic acid precipitating. It is cooled, filtered off with suction and washed with ethanol. 28.3 g (44.3% of theory) of a colourless compound of melting point >290° C. are obtained.

I claim:

1. A process for preparing 3-phenyl-quinoline-5-carboxylic acid having the formula

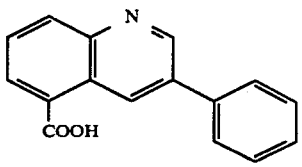

comprising reacting 4-amino-3-hydroxy-phthalide of the formula

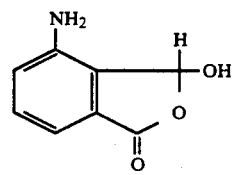

with phenylacetaldehyde.

* * * * *

UNITED STATES PATENT AND TRADEMARK OFFICE
CERTIFICATE OF CORRECTION

PATENT NO. : 5,270,469
DATED : December 14, 1993
INVENTOR(S) : Stoltefuss, Jurgen It is certified that error appears in the above-indentified patent and that said Letters Patent is hereby corrected as shown below:

```
Title Page & Col 1    [54] Title:  Line 1 delete " OF " and
line 1                sugstitute -- FOR--
```

Signed and Sealed this

Sixth Day of May, 1997

*Attest:*

BRUCE LEHMAN

*Attesting Officer*  *Commissioner of Patents and Trademarks*